United States Patent
Park et al.

(10) Patent No.: US 10,526,393 B2
(45) Date of Patent: *Jan. 7, 2020

(54) METHOD FOR PROMOTING VIRUS INFECTION AND INCREASING VIRUS PRODUCTION, BY USING CELL LINE HAVING LOST BST2 GENE FUNCTIONS

(71) Applicant: IMMUNOMAX CO., LTD., Seoul (KR)

(72) Inventors: Se-Ho Park, Seoul (KR); Eunbi Yi, Seoul (KR)

(73) Assignee: IMMUNOMAX CO., LTD., Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 15/318,665

(22) PCT Filed: Jun. 2, 2015

(86) PCT No.: PCT/KR2015/005493
§ 371 (c)(1),
(2) Date: Dec. 13, 2016

(87) PCT Pub. No.: WO2015/194770
PCT Pub. Date: Dec. 23, 2015

(65) Prior Publication Data
US 2017/0198025 A1   Jul. 13, 2017

(30) Foreign Application Priority Data

Jun. 18, 2014 (KR) ............ 10-2014-0074027
Sep. 2, 2014 (KR) ............ 10-2014-0116245

(51) Int. Cl.
| | |
|---|---|
| C12N 15/10 | (2006.01) |
| C12N 7/00 | (2006.01) |
| C07K 14/705 | (2006.01) |
| A61K 39/12 | (2006.01) |
| C07K 14/005 | (2006.01) |

(52) U.S. Cl.
CPC ........ C07K 14/70596 (2013.01); A61K 39/12 (2013.01); C07K 14/005 (2013.01)

(58) Field of Classification Search
None
See application file for complete search history.

(56) References Cited

U.S. PATENT DOCUMENTS

| | | | | |
|---|---|---|---|---|
| 8,546,123 B2* | 10/2013 | Lewis | ............ | A61K 39/13 435/235.1 |
| 9,650,613 B2* | 5/2017 | Park | ............ | C12N 7/00 |
| 2011/0027317 A1* | 2/2011 | Lewis | ............ | A61K 39/13 424/217.1 |
| 2012/0083035 A1 | 4/2012 | Spayd et al. | | |

FOREIGN PATENT DOCUMENTS

| | | | |
|---|---|---|---|
| EP | 2975119 A1 | | 1/2016 |
| JP | WO 2006008886 | * | 1/2006 |
| KR | 1020110029181 A | | 3/2011 |
| KR | 10-2012-0033334 A | | 4/2012 |
| KR | 10-2012-0103737 A | | 9/2012 |

OTHER PUBLICATIONS

Urata et al. Viruses 2012;4:2049-79.*
Hammonds et al. Mole Biol Intl 2012, Article ID 424768.*
Gupta et al. PloS Pathog 2009;5:e1000443.*
Swieckie et al. J Immunol 2012;188:2488-92.*
Jia et al Species-specific activity of siv nef and hiv-1 vpu in overcoming restriction by tetherin/bst2. PLoS Pathog. 2009, 5, e1000429; pp. 1-17.*
Zhang et al Nef proteins from simian immunodeficiency viruses are tetherin antagonists. Cell Host Microbe 2009, 6, 54-67.*
BST2 bone marrow stromal cell antigen 2 [ *Homo sapiens* (human) ] Gene—NCBI pp. 1-11; Downloaded Dec. 28, 2018.*
Winkler et al Influenza A Virus Does Not Encode a Tetherin Antagonist with Vpu-Like Activity and Induces IFN-Dependent Tetherin Expression in Infected Cells Aug. 27, 2012; e43337; pp. 1-9.*
en.wikipedia.org/wiki/vertebrates, last visited Dec. 28, 2018 pp. 1-10.*
waynesword.palomar.edu/trfeb98.htm, last visited Dec. 28, 2018 pp. 1-19.*
Londrigan et al Endogenous Murine BST-2/Tetherin Is Not a major Restriction Factor of Influenza A Virus Infection, PLOS ONE |2015; pp. 1-15.*
Le Tortorec et al., Antiviral Inhibition of Enveloped Virus Release by Tetherin/BST-2: Action and Counteraction Viruses 2011, 3, 520-540.*
Jang, J., et al., "Overexpression of Newcastle Disease Virus (NDV) V Protein Enhances NDV Production Kinetics in Chicken Embryo Fibroblasts", "Applied Microbiology and Biotechnology", Sep. 3, 2009, pp. 1509-1520, vol. 85.

(Continued)

*Primary Examiner* — Maria G Leavitt
(74) *Attorney, Agent, or Firm* — Hultquist, PLLC; Steven J. Hultquist

(57) ABSTRACT

The present invention relates to a method for promoting virus infection and increasing virus production, by using a cell line having lost Bst2 gene functions and, more specifically, to a method for promoting target virus infection and increasing target virus production, in addition to promoting virus budding and inhibiting host cell apoptosis by removing the Bst2 gene from a cell line having the ability to produce a virus. According to the present invention, the method for promoting target virus infection and increasing target virus production, by using an animal cell line having lost Bst2 gene functions, can improve production yields of a target virus and an antigen protein, and thus can be useful for the preparation of vaccines for treating and preventing viral diseases.

12 Claims, 4 Drawing Sheets
(1 of 4 Drawing Sheet(s) Filed in Color)
Specification includes a Sequence Listing.

(56) References Cited

OTHER PUBLICATIONS

Jones, P., et al., "Bone Marrow Stromal Cell Antigen 2 (BST-2) Restricts Mouse Mammary Tumor Virus (MMTV) Replication in Vivo", "Retrovirology", Jan. 27, 2012, pp. 1-12, vol. 9, No. 10.

Nguyen, N.Q.G., "Bone Marrow Stromal Antigen-2(BST-2): a Host Restriction Factor Against Murine γ-Herpesvirus (MHV68)", "Master's Thesis of Korea University Biotechnology Department", 2012.

Watanabe, R., et al., "Influenza Virus is Not Restricted by Tetherin whereas Influenza VLP Production is Restricted by Tetherin", "Virology", May 28, 2011, pp. 50-56, vol. 417.

Pan, X., et al., "BST2/Tetherin Inhibits Dengue Virus Release from Human Hepatoma Cells", "PLOS ONE", Dec. 7, 2012, pp. e51033 1-7, vol. 7, No. 12.

E. Yi, et al., "Enhanced Production of Enveloped Viruses in BST-2-Deficient Cell Lines", "Biotechnology and Bioengineering", Oct. 1, 2017, pp. 2289-2297, vol. 114, No. 10, Publisher: Wiley Periodicals, Inc.

* cited by examiner

METHOD FOR PROMOTING VIRUS INFECTION AND INCREASING VIRUS PRODUCTION, BY USING CELL LINE HAVING LOST BST2 GENE FUNCTIONS

CROSS-REFERENCE TO RELATED APPLICATIONS

This application is a U.S. national phase under the provisions of 35 U.S.C. § 371 of International Patent Application No. PCT/KR15/05493 filed Jun. 2, 2015, which in turn claims priority of Korean Patent Application No. 10-2014-0074027 filed Jun. 18, 2014 and Korean Patent Application No. 10-2014-0116245 filed Sep. 2, 2014. The disclosures of such international patent application and Korean priority patent applications are hereby incorporated herein by reference in their respective entireties, for all purposes.

TECHNICAL FIELD

The present invention relates to methods of promoting viral infection and viral production using a cell line lacking the function of Bst2 gene, and more particularly to a method of removing Bst2 gene from cells having the ability to produce virus, thereby promoting the release of virus from the cells, inhibiting the apoptosis of the cells, promoting the viral infection of the cells, and increasing the production of virus in the cells.

BACKGROUND ART

When virus infects the body, the proliferation of the virus in the infected cells occurs, and the proliferated virus particles bud out through the cell membrane to infect other surrounding cells. In part of the defense mechanism of cells against viral infection, Bst-2 tetherin) protein is expressed in the cell membrane. The Bst-2 protein has cell membrane-binding sites at both the N-terminus and the C-terminus, and thus is expressed in the cell membrane in a form in which the middle is lifted, like a bridge. The C-terminus of Bst-2 is located in the lipid raft region of the cell membrane, which is a specific region in which receptor activation occurs, and the N-terminus is located in the non-lipid raft region. When virus buds from the lipid raft region to the outside of the cells, the Bst-2 protein inhibits the passage of virus particles through the cell membrane by its region fixed to the non-lipid raft region. For this defense mechanism of mammal cells, some viruses produce a protein that promotes the degradation of the Bst-2 protein in order to avoid this mechanism of the host cells. This paradoxically indicates that the function of the Bst-2 gene strongly contributes to the inhibition of production of virus.

Until now, for the production of viruses for producing vaccines, a method of inoculating seed virus into fertilized eggs and culturing the inoculated virus has been used (KR 2012-0103737A). However, this method has very low efficiency due to problems, including allergic induction, the security of supply of fertilized eggs, and viral propagation. In an attempt to overcome such problems, methods of producing viral vaccines by animal cell culture have been used (KR 2012-0033334A). These methods include a method of producing a vaccine by culturing a large amount of animal cells under germ-free conditions and infecting the cultured animal cells with virus, a method of producing only antigens, which induce the production of antibodies against pathogens, by a genetic engineering method, etc. The biggest advantage of the method of producing vaccines by animal cell culture is that the production scale can be expanded. Specifically, the production scale can be expanded as desired according to the culture scale of animal cells that are used as a raw material for vaccine production.

However, despite such many advantages, the production of vaccines by animal cell culture is not easy to achieve. This is because the yield per unit volume is somewhat lower. In order to overcome low yields per unit volume when producing vaccines using animal cells, there were some attempts to develop excellent host animal cell lines using genetic engineering techniques (Jang J. et al., *Appl. Microbiol. Biotechnol* 85:1509-1520, 2010), but such attempts still remain at an insufficient level. Thus, to optimize virus production, the identification of a virus-producing cell line, the improvement of culture conditions and the improvement of infection conditions are required.

In previous studies, the present inventors found that when the function of Bst2 gene in a cell line having an ability to produce virus is lost, the release of the virus from the cell line is promoted so that the ability to produce the virus increases, and the apoptosis of the host cell is inhibited so that the stability of the virus-producing cell line increases (WO 2014142433).

Accordingly, the present inventors have made extensive efforts to find optimal methods for the production of virus and the production of a viral antigenic protein by improving the production yield of a target virus for producing a vaccine using an animal cell line, and as a result, have found that, if Bst2 protein in an animal cell line is removed, the release of virus from the animal cell line will be promoted, the apoptosis of the host cell will be inhibited, the viral infection of the host cell will be significantly promoted, and the production of a target virus will be increased, thereby completing the present invention.

DISCLOSURE OF INVENTION

Technical Problem

It is an object of the present invention to provide a method for promoting an infection of a target virus, the method comprising infecting a cell line which lacks the function of Bst2 gene and has the ability to produce virus, with a target virus.

Another object of the present invention is to provide a method for increasing a production of a target virus, the method comprising: infecting a cell line which lacks the function of Bst2 gene and has an ability to produce virus, with a target virus; and culturing the infected cell line.

Still another object of the present invention is to provide a method for producing an antigenic protein, the method comprising: infecting a cell line which lacks the function of Bst2 gene and has an ability to produce virus, with a target virus; and culturing the infected cell line.

Yet another object of the present invention is to provide a method for producing a vaccine against a viral disease, the method comprising using a viral antigenic protein produced by the above-described method.

Technical Solution

To achieve the above objects, the present invention provides a method for promoting an infection of a target virus, the method comprising infecting a cell line which lacks the function of Bst2 gene and has the ability to produce virus, with a target virus.

The present invention also provides a method for increasing a production of a target virus, the method comprising the steps of: infecting a cell line which lacks the function of Bst2 gene and has an ability to produce virus, with a target virus; and culturing the infected cell line.

The present invention also provides a method for producing an antigenic protein, the method comprising the steps of: infecting a cell line which lacks the function of Bst2 gene and has an ability to produce virus, with a target virus; and culturing the infected cell line.

The present invention also provides a method for producing a vaccine against a viral disease, the method comprising using a viral antigenic protein produced by the above-described method.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

BEST MODE FOR CARRYING OUT THE INVENTION

Figure 1:
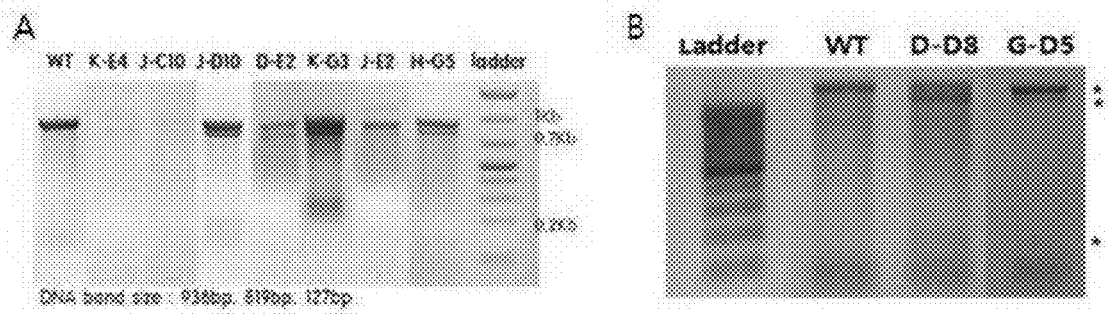
FIG. 1 shows the results of identifying mutations in cell lines (A: MDCK cell line; B: Vero cell line), which lack the function of Bst2 gene, by PCR followed by electrophoresis.

Unless defined otherwise, all technical and scientific terms used herein have the same meaning as commonly understood by one of ordinary skill in the art to which the invention pertains. Generally, the nomenclature used herein and the experiment methods, which will be described below, are those well known and commonly employed in the art.

In the present invention, it has been found that when Bst2 protein in an animal cell line is removed, the release of virus from the animal cell line is promoted, the apoptosis of the host cell is inhibited, the viral infection of the host cell is significantly promoted, and the production of a target virus and an antigenic protein is increased.

A cell line produced according to the method of the present invention is characterized in that it is easily infected with virus even when a smaller amount of virus and a shorter infection time are used, compared to a wild-type host cell, and in that it produces a protein of the infected virus in amounts larger than a wild-type host cell. In addition, the cell line produced according to the method of the present invention is characterized in that a virus produced in the cell line after infection is more easily released from the cell compared to that in a wild-type cell line and in that the virus-infected cell is a stable cell having resistance against apoptosis, which can produce the virus over an extended period of time. Accordingly, the methods for promoting an infection of the target virus and increasing the production of the target protein according to the present invention can increase the production yields of virus and antigenic protein, and thus are useful for the production of vaccines for the prevention or treatment of viral diseases.

In one aspect, the present invention is directed to a method for promoting an infection of a target virus, the method comprising infecting a cell line which lacks the function of Bst2 gene and has the ability to produce virus, with a target virus.

In the invention, the method for promoting viral infection increases the rate of infection with a target virus, and thus can be applied to develop a novel vaccine against a viral disease when a suitable cell line for culture of the virus does not exist.

In another aspect, the present invention is directed to a method for increasing a production of a target virus, the method comprising: infecting a cell line which lacks the function of Bst2 gene and has an ability to produce virus, with a target virus; and culturing the infected cell line.

In the present invention, "increasing a production of a target protein" refers to increasing the absolute production of a viral protein, that is, an antigenic protein.

In still another aspect, the present invention is directed to a method for producing an antigenic protein, the method comprising: infecting a cell line which lacks the function of Bst2 gene and has an ability to produce virus, with a target virus; and culturing the infected cell line.

In the present invention, the method for promoting an infection of a target virus and the method for increasing a production of the infected virus have an advantage in that they are capable of increasing the production of antigenic protein and maximizing the efficiency with which the antigenic protein is purified. In addition, according to the present invention, apoptosis is inhibited by viral infection so that the cell introduction cycle in the production of an antigenic protein can be minimized, and the release of viral particles into a culture medium is promoted so that the absolute production of an antigenic protein can also be increased.

As used herein, the term "ability to produce" means that a virus infect a host cell, and then is proliferated in the cell so that the virus is released into an extracellular culture medium.

As used herein, the term "lack of function" means mutating one or more nucleotides of Bst-2 gene in a cell, thereby promoting infection of a virus into the host cell, increasing production of a desired virus, promoting release of the virus into the extracellular culture medium, and inhibition of apoptosis of the host cell.

As used herein, the term "promoting infection" means mutating one or more nucleotides of Bst-2 gene in a cell, thereby enabling a small number of viruses to infiltrate the host cell within a short time.

As used herein, the term "promoting production" means mutating one or more nucleotides of Bst-2 gene in a cell, thereby increasing the amount of viral proteins in a cell per host cell.

As used herein, "antigenic protein" refers to a generic name of the antigen produced by an infected virus. These proteins are involved in the virulence or antigenicity of the virus and the host cell can recognize this, which shows the protective effect of the infection of the virus. The influenza virus particles have surface antigens defined as 16 kinds (H1 to H16) of the hemagglutinin (HA) and 9 kinds (N1 to N9) of neuraminidase (NA) and an S antigen (i.e., an antigen mainly defined as a ribonucleic protein NP antigen), and are divided into A type, B type, and C type by the serological specificity of the S antigen.

As used herein, the term "apoptosis" means a process in which a cell actively consumes the bioenergy ATP, leading to death. Apoptosis comprises the shrinkage of cells, the regular cleavage of DNA, and the fragmentation of the cell membrane, which are induced when cells cannot maintain their normal function due to abnormal cell division, radiation, UV light, bacterial infection or viral infection.

As used herein, the term "virus" means a virus that can cause a disease in humans or animals Preferably, the term means influenza and herpesvirus. More preferably, it means one selected from the group consisting of P/H1N1, A/H1N1, A/H3N2, and MHV68, but is not limited thereto.

In the present invention, the virus may be an enveloped or naked virus. Herein, the term "naked virus" refers to a virus consisting only of nucleic acid, protein or capsid, and the term "enveloped virus" refers to a virus having an envelope covering the capsid.

In the present invention, the virus may be a DNA or RNA virus. Herein, the DNA virus is a virus that have DNA as its genetic material, and examples thereof include ssDNA, dsDNA herpes virus), and circular DNA viruses. The RNA is a virus that has RNA as its genetic material, and examples thereof include (−)ssRNA (influenza virus), (+)ssRNA and dsRNA viruses.

In the present invention, the cell line having an ability to produce virus can be used irrespective of its kind as long as it is used to develop vaccines for the prevention or treatment of viral diseases. Preferably, an animal cell line may be used. More preferably, the cell line may be any one selected from the group consisting of a 293T human cell line, MDCK, Vero and a mouse fibroblast, but is not limited thereto.

MDCK (Madin-Darby Canine Kidney) cells that are used in the present invention are epithelioid cells derived from canine kidneys, and Vero cells that are used in the present invention are cells derived from monkey kidneys. The two types of cell lines are susceptible to hepatitis virus, vaccinia virus and influenza virus, and thus are most frequently used in viral production and research.

In the present invention, the cell line, which lacks the function of Bst2 gene and has an ability to produce virus, is preferably obtained either by deleting one or more nucleotides from the exon1 region of Bst2 gene or by inserting one or more nucleotides into the exon1 region of Bst2 gene that encodes the cytoplasmic domain of Bst2 protein, but is not limited thereto.

In the present invention, mutant cell lines were produced by deleting or inserting 1-15 nucleotides from or into the exon1 region of Bst2 gene, which is represented by SEQ ID NO: 1 or 2.

In an example of the present invention, 10 mutant cell lines, which comprise a mutated allele and have an increased ability to produce virus, were produced by deleting or inserting one or more nucleotides from or into the exon1 region of Bst2 gene of an MDCK cell line, which is represented by SEQ ID NO: 1.

```
                                        [SEQ ID NO: 1]
ATGGCACCTACGCTTTACCACTACTACTGGCCTGTGCCCATAACTGACGA

GTCAGAGTCAATGTCATCAAGTCAGAAGCTGAGCTGGCTGGAGTGGCTGG

GCATCTTGGGGATCCCAGTGGTGATGGGTCTGTCTGTGGCTCTGATCATC

TTTGTTGTCAAGACCAACAGCAAAGCCTGCGGGGATGGCCTCCTAGTAGA

GCAGGAGTGTCACAATGTCACCAGCCTCCTGGAGCGCCAACTAACCCAAA

CCCGGCAAGCGTTACAGGGGACCATGGACCAGGCTACCACCTGCAACAAG

ACTGTG
```

In an example of the present invention, mutant cell lines lacking the function of Bst2 gene were produced by deleting or inserting 1-10 nucleotides from or into positions 45 to 54 of SEQ ID NO: 1. These mutant cell lines may include cell lines having any one of nucleotide sequences of SEQ ID NOs: 3 to 8 and SEQ ID NOs: 17 to 21, and preferably may be K-E4, J-C10, J-D10, D-E2, K-G3, J-E2, H-G5, 8-D8, 14-F11 and 12-B8.

```
                                        [SEQ ID NO: 3]
ATGGCACCTACGCTTTACCACTACTACTGGCCTGTGCCCATAACTGA-AG

TCAGAGTCAATGTCATCAAGTCAGAAGCTGAGCTGGCTGGAGTGGCTGGG

CATCTTGGGGATCCCAGTGGTGATGGGTCTGTCTGTGGCTCTGATCATCT

TTGTTGTCAAGACCAACAGCAAAGCCTGCGGGGATGGCCTCCTAGTAGAG

CAGGAGTGTCACAATGTCACCAGCCTCCTGGAGCGCCAACTAACCCAAAC

CCGGCAAGCGTTACAGGGGACCATGGACCAGGCTACCACCTGCAACAAGA

CTGTG

[SEQ ID NO: 4]
ATGGCACCTACGCTTTACCACTACTACTGGCCTGTGCCCATAAC-ACGAG

TCAGAGTCAATGTCATCAAGTCAGAAGCTGAGCTGGCTGGAGTGGCTGGG

CATCTTGGGGATCCCAGTGGTGATGGGTCTGTCTGTGGCTCTGATCATCT

TTGTTGTCAAGACCAACAGCAAAGCCTGCGGGGATGGCCTCCTAGTAGAG

CAGGAGTGTCACAATGTCACCAGCCTCCTGGAGCGCCAACTAACCCAAAC

CCGGCAAGCGTTACAGGGGACCATGGACCAGGCTACCACCTGCAACAAGA

CTGTG

[SEQ ID NO: 5]
ATGGCACCTACGCTTTACCACTACTACTGGCCTGTGCCCATAACT----A

GTCAGAGTCAATGTCATCAAGTCAGAAGCTGAGCTGGCTGGAGTGGCTGG

GCATCTTGGGGATCCCAGTGGTGATGGGTCTGTCTGTGGCTCTGATCATC

TTTGTTGTCAAGACCAACAGCAAAGCCTGCGGGGATGGCCTCCTAGTAGA

GCAGGAGTGTCACAATGTCACCAGCCTCCTGGAGCGCCAACTAACCCAAA

CCCGGCAAGCGTTACAGGGGACCATGGACCAGGCTACCACCTGCAACAAG

ACTGTG

[SEQ ID NO: 6]
ATGGCACCTACGCTTTACCACTACTACTGGCCTGTGCCCATAACT---GA

GTCAGAGTCAATGTCATCAAGTCAGAAGCTGAGCTGGCTGGAGTGGCTGG
```

GCATCTTGGGGATCCCAGTGGTGATGGGTCTGTCTGTGGCTCTGATCATC

TTTGTTGTCAAGACCAACAGCAAAGCCTGCGGGGATGGCCTCCTAGTAGA

GCAGGAGTGTCACAATGTCACCAGCCTCCTGGAGCGCCAACTAACCCAAA

CCCGGCAAGCGTTACAGGGGACCATGGACCAGGCTACCACCTGCAACAAG

ACTGTG-3'

[SEQ ID NO: 7]
ATGGCACCTACGCTTTACCACTACTACTGGCCTGTGCCCATAAC----GA

GTCAGAGTCAATGTCATCAAGTCAGAAGCTGAGCTGGCTGGAGTGGCTGG

GCATCTTGGGGATCCCAGTGGTGATGGGTCTGTCTGTGGCTCTGATCATC

TTTGTTGTCAAGACCAACAGCAAAGCCTGCGGGGATGGCCTCCTAGTAGA

GCAGGAGTGTCACAATGTCACCAGCCTCCTGGAGCGCCAACTAACCCAAA

CCCGGCAAGCGTTACAGGGGACCATGGACCAGGCTACCACCTGCAACAAG

ACTGTG

[SEQ ID NO: 8]
ATGGCACCTACGCTTTACCACTACTACTGGCCTGTGCCCATAACTGACGA

CGAGTCAGAGTCAATGTCATCAAGTCAGAAGCTGAGCTGGCTGGAGTGGC

TGGGCATCTTGGGGATCCCAGTGGTGATGGGTCTGTCTGTGGCTCTGATC

ATCTTTGTTGTCAAGACCAACAGCAAAGCCTGCGGGGATGGCCTCCTAGT

AGAGCAGGAGTGTCACAATGTCACCAGCCTCCTGGAGCGCCAACTAACCC

AAACCCGGCAAGCGTTACAGGGGACCATGGACCAGGCTACCACCTGCAAC

AAGACTGTG

[SEQ ID NO: 17]
Atggcacctacgctttaccactactactggcctgtgcccataactgacct
atgagagtcagagtcaatgtcatcaagtcagaagctgagctggctggagt
ggctgggcatcttggggatcccagtggtgatgggtctgtctgtggctctg
atcatctttgttgtcaagaccaacagcaaagcctgcggggatggcctcct
agtagagcaggagtgtcacaatgtcaccagcctcctggagcgccaactaa
cccaaacccggcaagcgttacaggggaccatggaccaggctaccacctgc
aacaagactgtggtgaccctgtcagcttccctggtgaaggagaaggcctg
gggtcaggagcagctcacccgaggagagaaacttcagggagagatcgaga
cattgaagcagcagctgcaggccgctttggaggaggtgaagcagctaaga
gaagggaaggaggcctcaagcaaggaaagggaaaccagctccgtcagctc
cttgaaggcaccccggctccgtggtggtccccgtgtacctgctcctag
gccttagggctctgctggcctga

[SEQ ID NO: 18]
Atggcacctacgctttaccactactactggcctgtgcccataactga---
gtcagagtcaatgtcatcaagtcagaagctgagctggctggagtggctgg
gcatcttggggatcccagtggtgatgggtctgtctgtggctctgatcatc
tttgttgtcaagaccaacagcaaagcctgcggggatggcctcctagtaga
gcaggagtgtcacaatgtcaccagcctcctggagcgccaactaacccaaa
cccggcaagcgttacaggggaccatggaccaggctaccacctgcaacaag
actgtggtgaccctgtcagcttccctggtgaaggagaaggcctggggtca ggagcagctcacccgaggagagaaacttcagggagagatcgagacattga
agcagcagctgcaggccgctttggaggaggtgaagcagctaagagaaggg
aaggaggcctcaagcaaggaaagggaaaccagctccgtcagctccttgaa
ggcaccccggctccgtggtggtccccgtgtacctgctcctaggcctta
gggctctgctggcctga

[SEQ ID NO: 19]
Atggcacctacgctttaccactactactggcctgtgcccataactga-ga
gtcagagtcaatgtcatcaagtcagaagctgagctggctggagtggctgg
gcatcttggggatcccagtggtgatgggtctgtctgtggctctgatcatc
tttgttgtcaagaccaacagcaaagcctgcggggatggcctcctagtaga
gcaggagtgtcacaatgtcaccagcctcctggagcgccaactaacccaaa
cccggcaagcgttacaggggaccatggaccaggctaccacctgcaacaag
actgtggtgaccctgtcagctccctggtgaaggagaaggcctggggtca
ggagcagctcacccgaggagagaaacttcagggagagatcgagacattga
agcagcagctgcaggccgctttggaggaggtgaagcagctaagagaaggg
aaggaggcctcaagcaaggaaagggaaaccagctccgtcagctccttgaa
ggcaccccggctccgtggtggtccccgtgtacctgctcctaggcctta
gggctctgctggcctga

[SEQ ID NO: 20]
Atggcacctacgctttaccactactactggcctgtgcccataa-------
---agagtcaatgtcatcaagtcagaagctgagctggctggagtggctgg
gcatcttggggatcccagtggtgatgggtctgtctgtggctctgatcatc
tttgttgtcaagaccaacagcaaagcctgcggggatggcctcctagtaga
gcaggagtgtcacaatgtcaccagcctcctggagcgccaactaacccaaa
cccggcaagcgttacaggggaccatggaccaggctaccacctgcaacaag
actgtggtgaccctgtcagctccctggtgaaggagaaggcctggggtca
ggagcagctcacccgaggagagaaacttcagggagagatcgagacattga
agcagcagctgcaggccgctttggaggaggtgaagcagctaagagaaggg
aaggaggcctcaagcaaggaaagggaaaccagctccgtcagctccttgaa
ggcaccccggctccgtggtggtccccgtgtacctgctcctaggcctta
gggctctgctggcctga

[SEQ ID NO: 21]
Atggcacctacgctttaccactactactggcctgtgcccata---gacga
---agagtcaatgtcatcaagtcagaagctgagctggctggagtggctgg
gcatcttggggatcccagtggtgatgggtctgtctgtggctctgatcatc
tttgttgtcaagaccaacagcaaagcctgcggggatggcctcctagtaga
gcaggagtgtcacaatgtcaccagcctcctggagcgccaactaacccaaa
cccggcaagcgttacaggggaccatggaccaggctaccacctgcaacaag
actgtggtgaccctgtcagctccctggtgaaggagaaggcctggggtca
ggagcagctcacccgaggagagaaacttcagggagagatcgagacattga
agcagcagctgcaggccgctttggaggaggtgaagcagctaagagaaggg
aaggaggcctcaagcaaggaaagggaaaccagctccgtcagctccttgaa -continued

```
ggcacccccggctccgtggtggtccccgtgtacctgctcctaggcctta gggctctgctggcctga
```

In an example of the present invention, the nucleotide sequences of the produced mutant cell lines were analyzed, and as a result, it could be seen that a frameshift mutation in the alleles of K-E4, J-C10, J-D10 and 14-F11 cells from MDCK cells occurred.

As used herein, the term "frameshift mutation" means a deletion or insertion of 1, 2 or more nucleotides (other than a multiple of 3) that result in a change in a frameshift that can read a genetic code of three nucleotides.

Among the mutant cell lines, J-D10 was deposited under the accession number KCLRF-BP-00285.

In another example of the present invention, 2 mutant cell lines, which comprise a mutated allele and have an increased ability to produce virus, were produced by deleting one or more nucleotides from the exon1 region of Bst2 gene of a Vero cell line, which is represented by SEQ ID NO: 2.

```
                                             [SEQ ID NO: 2]
ATGGCACCTATTTTGTATGACTATTGCAAAATGCCCATGGATGACATTTG

CAAGGAAGACAGGGACAAGTGCTGTAAACTGGCCGTAGGAATTCTGGGGC

TCCTGGTCATAGTGCTTCTGGGGGTGCCCCTGATTTTCTTCATCATCAAG

GCCAACAGCGAGGCCTGCCAGGATGGCCTCCGGGCAGTGATGGAGTGTCA

CAATGTCACCTATCTCCTGCAACAAGAGCTGGCCGAGGCCCAGCGGGGCT

TTCGGGACGCAGAGGCCCAGGCTGTCACCTGCAACCAGACTGTG
```

In an example of the present invention, mutant cell lines lacking the function of Bst2 gene were produced by deleting 1-12 nucleotides from positions 116 to 130 of SEQ ID NO: 2. These mutant cell lines may include cell lines having any one of nucleotide sequences of SEQ ID NOs: 9 and 10, and preferably may be D-D8 and G-D5.

```
                                             [SEQ ID NO: 9]
ATGGCACCTATTTTGTATGACTATTGCAAAATGCCCATGGATGACATTTG

CAAGGAAGACAGGGACAAGTGCTGTAAACTGGCCGTAGGAATTCTGGGGC

TCCTGGTCATAGTGC------------CCCTGATTTTCTTCATCATCAAG

GCCAACAGCGAGGCCTGCCAGGATGGCCTCCGGGCAGTGATGGAGTGTCA

CAATGTCACCTATCTCCTGCAACAAGAGCTGGCCGAGGCCCAGCGGGGCT

TTCGGGACGCAGAGGCCCAGGCTGTCACCTGCAACCAGACTGTG

[SEQ ID NO: 10]
ATGGCACCTATTTTGTATGACTATTGCAAAATGCCCATGGATGACATTTG

CAAGGAAGACAGGGACAAGTGCTGTAAACTGGCCGTAGGAATTCTGGGGC

TCCTGGTCATAGTGCTTCTGGGGGTGCCCTGATTTTCTTCATCATCAAGG

CCAACAGCGAGGCCTGCCAGGATGGCCTCCGGGCAGTGATGGAGTGTCAC

AATGTCACCTATCTCCTGCAACAAGAGCTGGCCGAGGCCCAGCGGGGCTT

TCGGGACGCAGAGGCCCAGGCTGTCACCTGCAACCAGACTGTG
```

In another example of the present invention, 3 mutant cell lines, which comprise a mutated allele and have an increased ability to produce virus, were produced by deleting or inserting one or more nucleotides from or into the exon1 region of Bst2 gene of the 293T human cell line, which is represented by SEQ ID NO: 24.

```
                                            [SEQ ID NO: 24]
ATGGCATCTACTTCGTATGACTATTGCAGAGTGCCCATGGAAGACGGGGA

TAAGCGCTGTAAGCTTCTGCTGGGGATAGGAATTCTGGTGCTCCTGATCA

TCGTGATTCTGGGGGTGCCCTTGATTATCTTCACCATCAAGGCCAACAGC

GAGGCCTGCCGGGACGGCCTTCGGGCAGTGATGGAGTGTCGCAATGTCAC

CCATCTCCTGCAACAAGAGCTGACCGAGGCCCAGAAGGGCTTTCAGGATG

TGGAGGCCCAGGCCGCCACCTGCAACCACACTGTGGTAAGCTCCTCAACT

CCTTTGGATGGCCTAGTACTAGGCGGTGGGAGGGACAAGAATCTCTCCCC

AGAAATCTGACCCAGGGTGGGTCTCCAGGGAGATGCAGGGGAGGTCCTGA

AACTGCTCCTGGGCCCCCACATCAAGGGACCTAGGTTCCCCTACCAGGGT

TTGTGGGCCCCTAACCCAGTCCAGGGCACTGGTGTAGGGGCAGGGTGTTA

AAACTCTCCAGATCCCCCAAATCGGGGACCTCAGTATCCCCCTGGGACTT

AGGTGAATTTATAAATTCTTTCCAGGGCACTGGTGTCGGGGGCCTTGAAA

CTCCTCGTGGGCACCAGTCCTGGGGGAGTAGAAATCCCTATTCAGGGTTG

AAGGGGGACCTCACCAGACCCTGAAAAAGGGGGCTTTTGAAATTTTCACT

TCATCCCTAAGAAACTGAAATATTCACCTGGGTCCTGATATGGGGGATCT

TGAAACTCTCGCTGGGCATGTCACTTGGGCGGGGAAATCCCACTGCATTC

TGGATTTGGTAGGGCCCTCTAACTTTTCTTGGGCCATTGCTCAGGCAATC

TGGAAATGTCCACTAAACTTTGGTTATCGATAGCCTCCAAGTTTCCACGT

GGGGTGGCCTCAAAACTCCCATTTTGAGGACCCACATGCTTATGGGTGGC

CCTGGGAGAGTGTGTGGTTGTGGCTGTTCTTTAAGGTTGGAGACCATGGT

GCAGAGAGGGTTGGAAGAAAACCTGAAAGGGGTTTGCATTTAAGCCCCTC

TGTCCCCAGGACCTAGGGAGGAGGCCCAGGTCCCAGGGGCAGCAGCCAAA

CTCCCCAGGCCAAAACCCCAGATTCTAACTCTTCTTAGATGGCCCTAATG

GCTTCCCTGGATGCAGAGAAGGCCCAAGGACAAAAGAAAGTGGAGGAGCT

TGAGGGTGAGAAAGGGAGAAGGGAGAGGGCCGGGGAGGGGTGAGTCAGGT

ATGGAAGAGGGGGTGGGGGCAGGGAGACCAGGGCTGGAGGTTGGGGTAAG

GGGGAGGTTCTGTCCCAGAGTGGAGCAGGGCCCCAGCATGGCCACATGCT

GACCCGCCCCCTGTTTCTGTCCTCCCACCCTACCAGGAGAGATCACTACA

TTAAACCATAAGCTTCAGGACGCGTCTGCAGAGGTGGAGCGACTGAGGTC

AGAGATAGCCTTCCCCCGCTACCCTCCACCTGCCACATTCCTCTCACCCC

CACATCCCTAGCCCAAGACCCAGGATCTCCTTTGCTCCCAAAATCCCCAT

TGCCCCAAGGGATAAAGTTTGAGTCCCACAAAAGGATAACTTAGCCCCTA

GGGTCACAGAGCCATGGGTGGCCGCTGTCCATTCCCTCCCCGGTGACTTG

GATTGGGGCGGTGCGGGGGGAACTCCCGGGGGCGGTGGGCTTACAGGGAG

GGCGGCAGGAGCCAGGACGAGCAGATGCCTGATTTGCCATCTGTACCGCA

GAAGAGAAAACCAGGTCTTAAGCGTGAGAATCGCGGACAAGAAGTACTAC

CCCAGCTCCCAGGACTCCAGCTCCGCTGCGGCGCCCCAGCTGCTGATTGT

GCTGCTGGGCCTCAGCGCTCTGCTGCAGTGA
```

In an example of the present invention, mutant cell lines lacking the function of Bst2 gene were produced by deleting 3-27 nucleotides from or inserting 1 nucleotide into positions 51 to 100 of SEQ ID NO: 24. These mutant cell lines may include cell lines having any one of nucleotide sequences of SEQ ID NOs: 25 to 30, and preferably may be D-19, B4 and B24.

[SEQ ID NO: 25]
ATGGCATCTACTTCGTATGACTATTGCAGAGTGCCCATGGAAGACGGGGA

---------------------------GATAGGAATTC

[SEQ ID NO: 26]
ATGGCATCTACTTCGTATGACTATTGCAGAGTGCCCATGGAAGACGGGGA

TAAGCGCTGTAAGCTTCTGCTGGGGATAGGAATTC------

[SEQ ID NO: 27]
ATGGCATCTACTTCGTATGACTATTGCAGAGTGCCCATGGAAGACGGGGA

TAAGCGCTGTAAGCTTC<u>t</u>TGCTGGGGATAGGAATTC

[SEQ ID NO: 28]
ATGGCATCTACTTCGTATGACTATTGCAGAGTGCCCATGGAAGACGGGGA

TAAGCGCTGTAAGC--------------------

[SEQ ID NO: 29]
ATGGCATCTACTTCGTATGACTATTGCAGAGTGCCCATGGAAGACGGGGA

TAAGCGCTGTAAGCTTCTGCTGATAGGAATTC---

[SEQ ID NO: 30]
ATGGCATCTACTTCGTATGACTATTGCAGAGTGCCCATGGAAGACGGGGA

TAAGCGCTGTAA--------TGGGGATAGGAATTC

In the methods of promoting viral infection and increasing viral production using a cell line lacking the function of Bst2 gene according to the present invention, the number of cells used may be $1\times10^4$ to $1\times10^7$, preferably $5\times10^4$ to $5\times10^6$, more preferably $1\times10^5$ to $1\times10^6$.

Virus inoculated into the cells is preferably infected at an MOI of 0.0001-0.1 in a 5% $CO_2$ incubator at 37° C., but is not limited thereto. The infected virus may be cultured in a fresh medium for 36-72 hours, and the medium may be removed. The remaining cells may be centrifuged under suitable conditions, and the supernatant may be collected and centrifuged at 1500-5000 rpm and 4° C. to 15° C. for 15 minutes, followed by collection of the supernatant.

In an example of the present invention, a viral antigenic protein was produced by infecting a cell line which lacks the function of Bst2 gene and having an ability to produce virus, with a target virus, followed by culture to increase the production f the target virus. The viral antigenic protein may be used for production of a vaccine against for the prevention or treatment of a viral disease.

Therefore, in yet another aspect, the present invention is directed to a method for producing a vaccine against a viral disease, the method comprising using a viral antigenic protein produced by the above-described method.

The vaccine composition may further contain a pharmaceutically acceptable adjuvant or excipient. Any adjuvant may be used as long as it can serve to promote formation of an antibody at the time of injecting the adjuvant into the body to achieve the objects of the present invention. Particularly, the adjuvant that can be used in the present invention is preferably at least one selected from among aluminum ($Al(OH)_3$, or $AlPO_4$), squalene, sorbitane, polysorbate 80, CpG, liposome, cholesterol, monophosphoryl lipid (MPL) A, and glucopyranosyl lipid (GLA) A., but is not limited thereto.

EXAMPLES

Hereinafter, the present invention will be described in further detail with reference to examples. It will be obvious to a person having ordinary skill in the art that these examples are illustrative purposes only and are not to be construed to limit the scope of the present invention.

Example 1

Cell Lines Lacking the Function of Bst2 Gene 1-1: MDCK Cell Line $5\times10^5$ wild-type MDCK cells obtained from Professor Moon-Jung Song (Korea University, Korea) were cultured in DMEM complete (GIBCO) medium (containing 10% FBS, and 2 mM L-glutamine, 5M β-mercaptoethanol, 10 μg/ml gentamicine, 50 U/ml penicillin, and 50 μg/ml streptomycin) for 24 hours. Then, 15 μg of a mixture of a pair of TALEN vectors (ToolGen, Korea) capable of binding to the exon 1 region of the Bst2 gene, one reporter vector (ToolGen, Korea) and Turbofect reagent, was added to the cultured cells which were then incubated under the conditions of 37° C. and 5% $CO_2$ for 48 hours. The cultured cells were sorted by FACS Aria (BD Bioscience) to select 500 cells positive to both GFP and RFP, and the selected cells were seeded in a 96-well plate, thereby obtaining monoclonal cells.

In order to confirm a mutation in the obtained monoclonal cells, the genomic DNA was extracted and subjected to polymerase chain reaction (PCR) using a dBst-2-F primer represented by SEQ ID NO: 11 and a dBst-2-R primer represented by SEQ ID NO: 12 under the following conditions: 95° C. for 5 min, and then 25 cycles, each consisting of 94° C. for 30 sec, 60° C. for 30 sec and 72° C. for 1 min, followed by 72° C. for 10 min. The reaction product was diluted to $10^{-3}$, and subjected to PCR using an NdBst-2-F primer represented by SEQ ID NO: 13 and an NdBst-2-F primer represented by SEQ ID NO: 14 under the following conditions: 95° C. for 5 min, and then 25 cycles, each consisting of 94° C. for 30 sec, 60° C. for 30 sec and 72° C. for 1 min, followed by 72° C. for 10 min.

[SEQ ID NO: 11]
5'-GGTCAGGATGGCTCCTATGC-3'

[SEQ ID NO: 12]
5'-AACCTGACAGGGTCACCTGG-3'

[SEQ ID NO: 13]
5'-GTAGCCCCAGCCAAAGGTTTC-3'

[SEQ ID NO: 14]
5'-AGGCCTCCCCATGCCCAAAC-3'

The size of the reaction product was analyzed by electrophoresis. As a result, it was shown that the cell lines having a putative mutation in the exon 1 region represented by SEQ ID NO: 1 had a normal PCR reaction product size and two additional bands caused by cleavage with endonuclase, indicating that a mutation in the exon 1 region occurred (FIG. 1, panel A).

To analyze the nucleotide sequences of the cell lines confirmed to have a mutation, the PCR reaction product treated with T7E1 enzyme (ToolGen, Korea) was digested with Bgl-Xba, ligated with a pUC18 vector, and then cultured in a medium containing ampicillin and X-gal-IPTG, thereby obtaining white colonies. Among the obtained white colonies, 6 colonies were selected for each clone and sequenced.

As a result, it was shown that, among 7 mutant cell lines (K-E4, J-C10, J-D10, D-E2, K-G3, J-E2 and H-G5) having a deletion or insertion of nucleotides in the exon 1 region of Bst2, 3 mutant cell lines (K-E4, J-C10 and J-D10) had a frameshift mutation that occurred in a pair of alleles.

1-2: Vero Cell Line $5 \times 10^5$ wild-type VERO cells (University of Southern California, Chengyu Liang) were cultured in DMEM complete (GIBCO) medium (containing 10% FBS, 2 mM L-glutamine, 5M β-mercaptoethanol, 10 μg/ml gentamicine, 50 U/ml penicillin, and 50 μg/ml streptomycin) for 24 hours. Then, 15 μg of a mixture of a pair of TALEN vectors (ToolGen, Korea) capable of binding to the exon 1 region of the Bst2 gene, one reporter vector (ToolGen, Korea) and Turbofect reagent (Thermo, USA), was added to the cultured cells which were then incubated under the conditions of 37° C. and 5% $CO_2$ for 48 hours. The cultured cells were sorted by FACS Aria (BD Bioscience) to select 500 cells positive to both GFP and RFP, and the selected cells were seeded in a 96-well plate, thereby obtaining monoclonal cells.

In order to confirm a mutation in the obtained monoclonal cells, the genomic DNA was extracted and subjected to polymerase chain reaction (PCR) using a dBst-2-F primer represented by SEQ ID NO: 11 and an AGM-R primer represented by SEQ ID NO: 16 under the following conditions: 95° C. for 5 min, and then 25 cycles, each consisting of 94° C. for 30 sec, 60° C. for 30 sec and 72° C. for 1 min, followed by 72° C. for 10 min. The reaction product was diluted to $10^{-3}$, and subjected to PCR using an AGM-F primer represented by SEQ ID NO: 15 and an AGM-R primer represented by SEQ ID NO: 16 under the following conditions: 95° C. for 5 min, and then 25 cycles, each consisting of 94° C. for 30 sec, 60° C. for 30 sec and 72° C. for 1 min, followed by 72° C. for 10 min.

[SEQ ID NO: 15]
5'-GAGGGGGAGATCTGGATGG-3'

[SEQ ID NO: 16]
5'-CTTCTCTGCATCCAGGGAAG-3'

The size of the reaction product was analyzed by electrophoresis. As a result, it was shown that two cell lines having a putative mutation in the exon 1 region had a normal PCR reaction product size and two additional bands caused by cleavage with endonuclease, indicating that a mutation in the exon 1 region occurred (FIG. 1, panel B).

The nucleotide sequences of the cell lines confirmed to have a mutation were analyzed, and as a result, 2 mutant cell lines (D-D8: hetero; and G-D5: knockout) having a deletion or insertion of nucleotides in the exon 1 region of Bst2 were identified.

1-3: Fibroblast Cell Line B2K

To produce a mouse fibroblast cell line (B2K) lacking Bst2, 100 μg of MCA (3-methyl cholanthrene) was injected into the thigh of 24-week-old Bst2 knockout mice (ISU Abxis, Korea). After about 4 months, a tumor formed in the thigh was detached and washed with 70% ethanol to remove bacteria, after which it transferred into a dish containing 10% FBS and RPMI medium and was cut into fine pieces using surgical scissors. The tumor pieces and 13 ml of digestion solution (500 Unit/ml collagenase IV, 150 Unit/ml DNase I) were placed in a 50-ml conical tube and shaken in a shaker at 250 rpm and 37° C. for 1 hour and 30 minutes. The shaken solution was pipetted 3-5 times with a 10-ml pipette to further disperse the pieces, and then filtered through a nylon mesh and placed in a 50-ml fresh conical tube. Then, the resulting solution was centrifuged at 1250 rpm for 5 minutes, and the supernatant was removed, after which the pellets were suspended in a fresh medium, filtered through a nylon mesh, and centrifuged under the above-described conditions. After removal of the supernatant, the pellets were dissociated, seeded at a density of $2.4 \times 10^7$ cells per 10 cm dish, and cultured to obtain a knockout tumor cell line (B2K).

Meanwhile, to produce a wild-type tumor cell line (MB19), 100 μg of MCA (3-methyl cholanthrene) was injected into the thigh of 24-week-old B6 wild-type mice (Orient Bio, Korea). After about 4 months, a tumor formed in the thigh was detached and washed with 70% ethanol to remove bacteria, after which it transferred into a dish containing 10% FBS and RPMI medium and was cut into fine pieces using surgical scissors. The tumor pieces and 13 ml of digestion solution (500 Unit/ml collagenase IV, 150 Unit/DNase I) were placed in a 50-ml conical tube and shaken in a shaker at 250 rpm 37° C. for 1 hour and 30 minutes. The shaken solution was pipetted 3-5 times with a 10-ml pipette to further disperse the pieces, and then filtered through a nylon mesh and placed in a 50-ml fresh conical tube. Then, the resulting solution was centrifuged at 1250 rpm for 5 minutes, and the supernatant was removed, after which the pellets were suspended in a fresh medium, filtered through a nylon mesh, and centrifuged under the above-described conditions. After removal of the supernatant, the pellets were dissociated, seeded at a density of $2.4 \times 10^7$ cells per 10 cm dish, and cultured to obtain a wild-type tumor cell line (MB19).

The MHC class (KbDb(R1.21.2)-APC, CD1d(1B1)-PE), LFA-1(207)-Cyc, and Bst2(e.Bio927)biotin+Streptavidin-PE of each of the Bst2 knockout tumor cell line (B2K) and the Bst2 wild-type tumor cell line (MB19) was fluorescence-stained, and the expression levels thereof were compared.

As a result, it was observed that MB19 normally expressed Bst2, whereas the B2K tumor cell line did not express Bst2. Thus, the B2K tumor cell line was used in the following Example.

1-4: Human 293T Cell Line $5 \times 10^5$ human 293T cells were cultured in DMEM complete (GIBCO) medium (containing 10% FBS, 2 mM L-glutamine, 5M β-mercaptoethanol, 10 μg/ml gentamicine, 50 U/ml penicillin, and 50 μg/ml streptomycin) for 24 hours. Then, 18 μg of a mixture of one CRISPR vector (ToolGen, Korea) capable of binding to the exon 1 region of the Bst2 gene, one reporter vector(ToolGen, Korea), a Cas9 vector and Fugene (Promega, USA), was added to the cultured cells which were then incubated under the conditions of 37° C. and 5% $CO_2$ for 48 hours. The cultured cells were sorted by FACS Aria (BD Bioscience) to select 500 cells positive to both GFP and RFP, and the selected cells were seeded in a 96-well plate, thereby obtaining monoclonal cells.

In order to confirm a mutation in the obtained monoclonal cells, the genomic DNA was extracted and subjected to polymerase chain reaction (PCR) using a HBst2-F1 primer represented by SEQ ID NO: 22 and a HBst2-R1 primer represented by SEQ ID NO: 23 under the following conditions: 95° C. for 3 min, then 10 cycles, each consisting of 94° C. for 30 sec, 72° C. for 30 sec, and 72° C. for 45 sec, followed by 25 cycles, each consisting of 95° C. for 30 sec, 62° C. for 30 sec, and 72° C. for 45 sec.

[SEQ ID NO: 22]
5'-TGG CAC GGC CTA GGC ACT CA-3'

[SEQ ID NO: 23]
5'-GGA TAC TGA GGT CCC CGA TT-3'

The size of the reaction product was analyzed by electrophoresis, and then the nucleotide sequences of the cell lines confirmed to have a mutation were analyzed. As a result, 3 mutant cell lines (D19 Allele 1: 27 nucleotides deleted, D19 Allele 2: 6 nucleotides deleted, B4 Allele 1: 1 nucleotide inserted, B4 Allele 2: 21 nucleotides deleted, B24 Allele 1: 3 nucleotides deleted, B24 Allele 2: 8 nucleotides deleted) having a deletion or insertion of nucleotides in the exon 1 region of Bst2 were identified.

Example 2

Promotion of Infection of Cell Line Lacking Bst2 Gene 2-1: Infection with Low MOI of Virus To confirm the effect of promoting the infection of a cell line lacking the function of Bst2 gene, the viral infection of cell lines lacking the function of Bst2 was compared with that of a wild-type MDCK cell line. In this Example, 8-D8, 14-F11 and 12-B8, each comprising a mutated allele, were used which are cell lines having a frameshift mutation that occurred in the exon1 region of the Bst2 to completely silence the expression of the Bst2 gene, in the same manner as the J-D10 (accession number KCLRF-BP-00285) cell line obtained in Example 1. The mutation sequences of 8-D8, 14-F11 and 12-B8 are represented by SEQ ID NOs: 17 to 21. Specifically, 8-D8 comprises mutated alleles of SEQ ID NOs: 17 and 18; 14-F11 comprises mutated alleles of SEQ ID NOs: 19 and 20; and 12-B8 comprises mutated alleles of SEQ ID NOs: 18 and 21.

Each type of wild-type MDCK cells and cells ($5\times10^4$ cell/well) lacking the function of Bst2 was injected for 30 minutes with A/H3N2 influenza virus that had been diluted serially 2-fold from an MOD of 0.001. Then, the medium was removed, and the cell layer was covered with agarose, after which the infected virus was grown for 48 hours.

Figure 2:
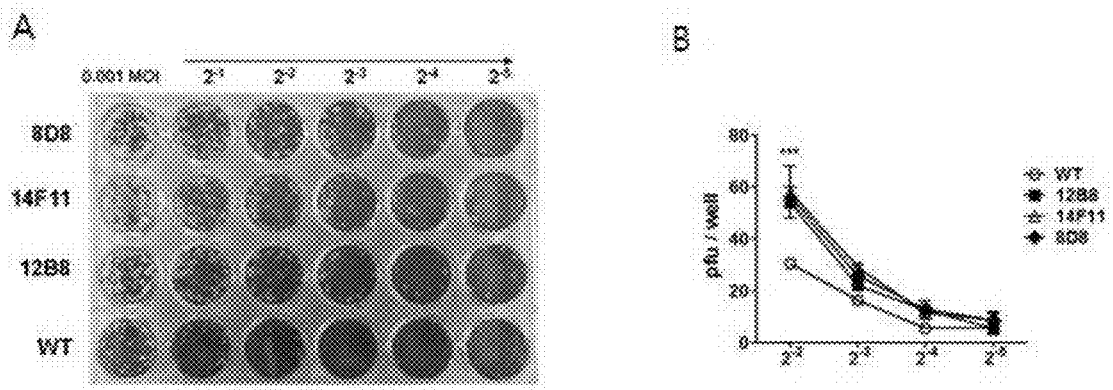
FIG. 2 shows the results of comparing infectivity between a wide-type cell line and cell lines lacking the function of Bst2 gene as a function of MOI.

As a result, it was shown that the cell lines lacking the function of Bst2 were infected with the same efficiency as the wild-type cell line, even though the number of virus particles that infected the cell lines lacking the function of Bst2 was about ⅕ of the number of virus particles that infected the wild-type cell line (FIG. 2). This suggests that removal of the Bst2 protein from host cells promotes the infection of the host cells with virus.

2-2: Reduction in Viral Infection Time

Each type of wild-type MDCK cells and cells ($5\times10^4$ cell/well) lacking the function of Bst2 was infected with 0.0001 MOI of A/H3N2 influenza virus for 1 min, 5 min, 10 min, 20 min, 30 min and 1 hour. Then, the medium was removed, and the cell layer was covered with agarose, after which the infected virus was grown for 48 hours.

Figure 3:
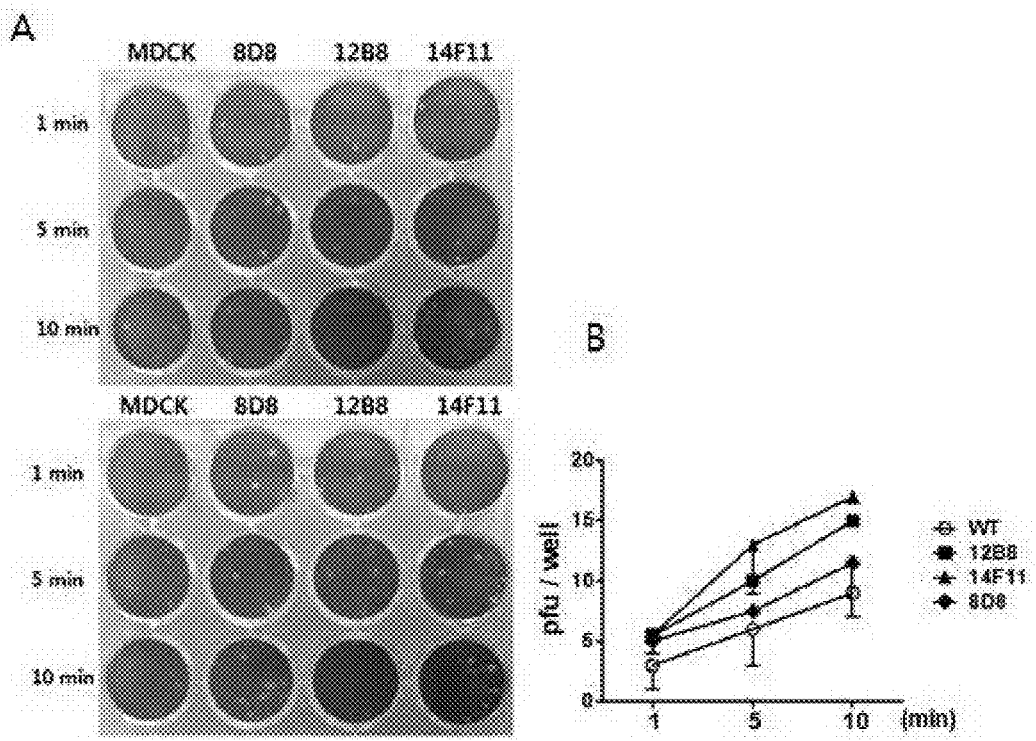
FIG. 3 shows the results of comparing infectivity between a wide-type cell line and cell lines lacking the function of Bst2 gene as a function of infection time.
Figure 4:
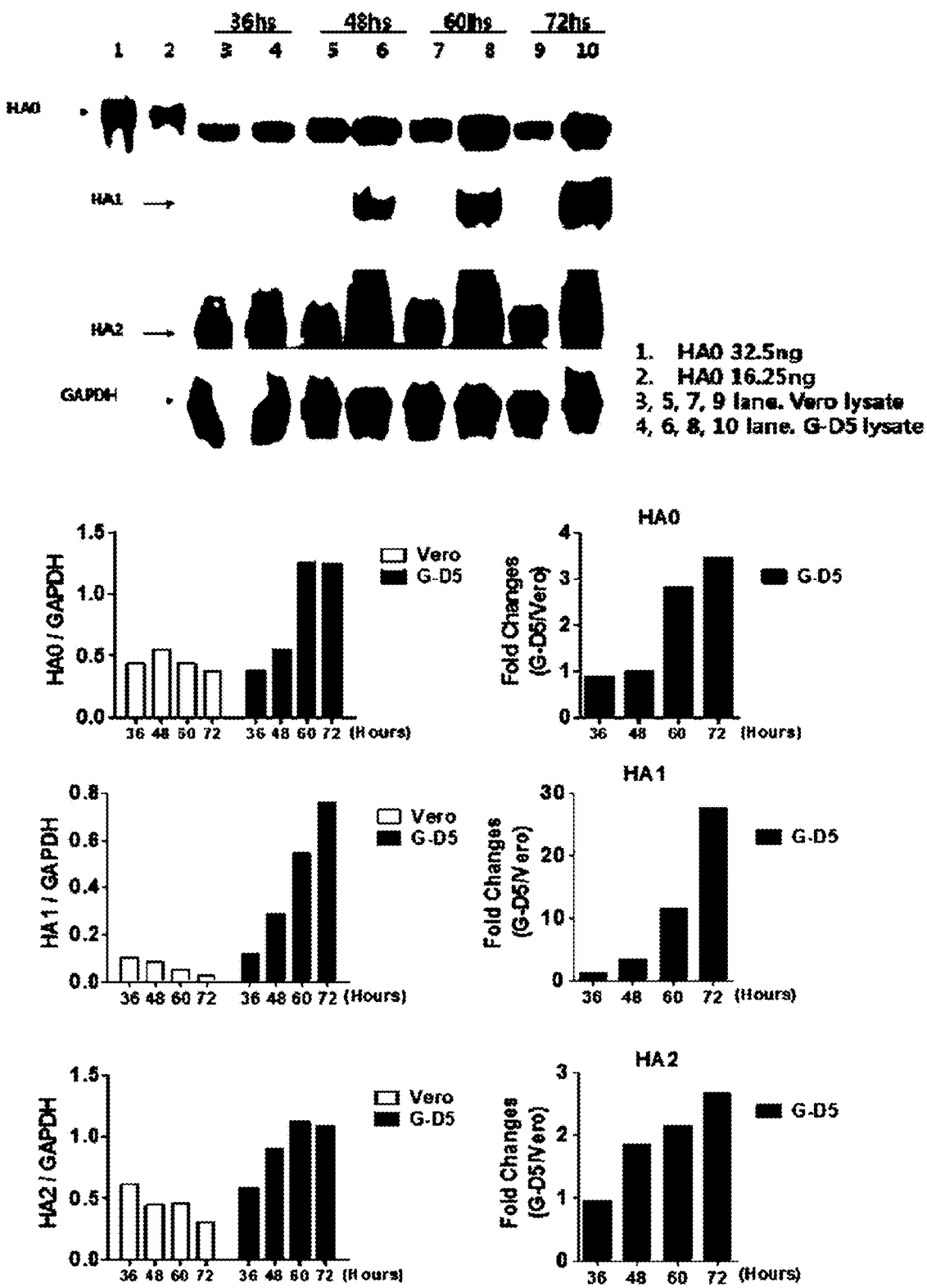
FIG. 4 shows the results of comparing the increase in intracellular viral antigenic proteins in total cell lysates between a wild-type Vero cell line and a G-D5 cell line lacking the function of Bst2 gene.

As a result, plaque formation in the cell lines lacking the function of Bst2 was 3-6 pfu/well at 1 min, which was 1.8 times higher than that in the wild-type cell line, 6-10 pfu/well at 5 min, which was 1.7 times higher than that in the wild-type cell line, and 9-14 pfu/well at 10 min, which was about 1.5 times higher than that in the wild-type cell line (FIG. 3). At a sufficient infection time of 20 minutes or more, there was no difference in plaque formation between the wild-type MDCK cells and the cells lacking the function of Bst2.

This suggests that virus can more easily penetrate cells lacking the function of Bst2 within a shorter time and that the viral infectivity of a cell line lacking the function of Bst2 is significantly higher than that of a wild-type cell line. Accordingly, it was found that the Bst2 protein not only inhibits the extracellular release of virus as reported previously, but also inhibits the penetration of virus into a host cell. Namely, it can be seen that removal of the function of Bst2 from cells increases the rate of the cells with a target virus to thereby promote the infection of the cells with the target virus.

Example 3

Increase in the Amount of Intracellular Viral Protein in Cell Lines Lacking the Function of Bst2 Gene 3-1: Vero and MDCK Cell Lines To confirm an increase in the production of viral antigenic proteins in cell lines lacking the function of Bst2 gene, the production of viral antigenic proteins was compared between wild-type Vero and MDCK cell lines and cell lines lacking the function of Bst2. In this Example, the G-D5 and J-D10 (accession number KCLRF-BP-00285) cell lines obtained in Example 1 were used.

Wild-type Vero and MDCK cells and cells ($5\times10^4$ cell/well) lacking the function of Bst2 were infected with 0.1 MOI of A/H3N2 influenza virus for 30 minutes, and then the medium was replaced with a refresh medium, followed by culture for 36-72 hours. At each time point, viruses released into the medium were removed, and the cells remaining at the bottom of the culture flask were washed with PBS, and then harvested, thereby obtaining cell lysates. The obtained cell lysates were electrophoresed by SDS-PAGE, and then analyzed by Western blotting with anti-HA monoclonal antibody that recognizes large fragments of influenza virus HA proteins.

Figure 5:
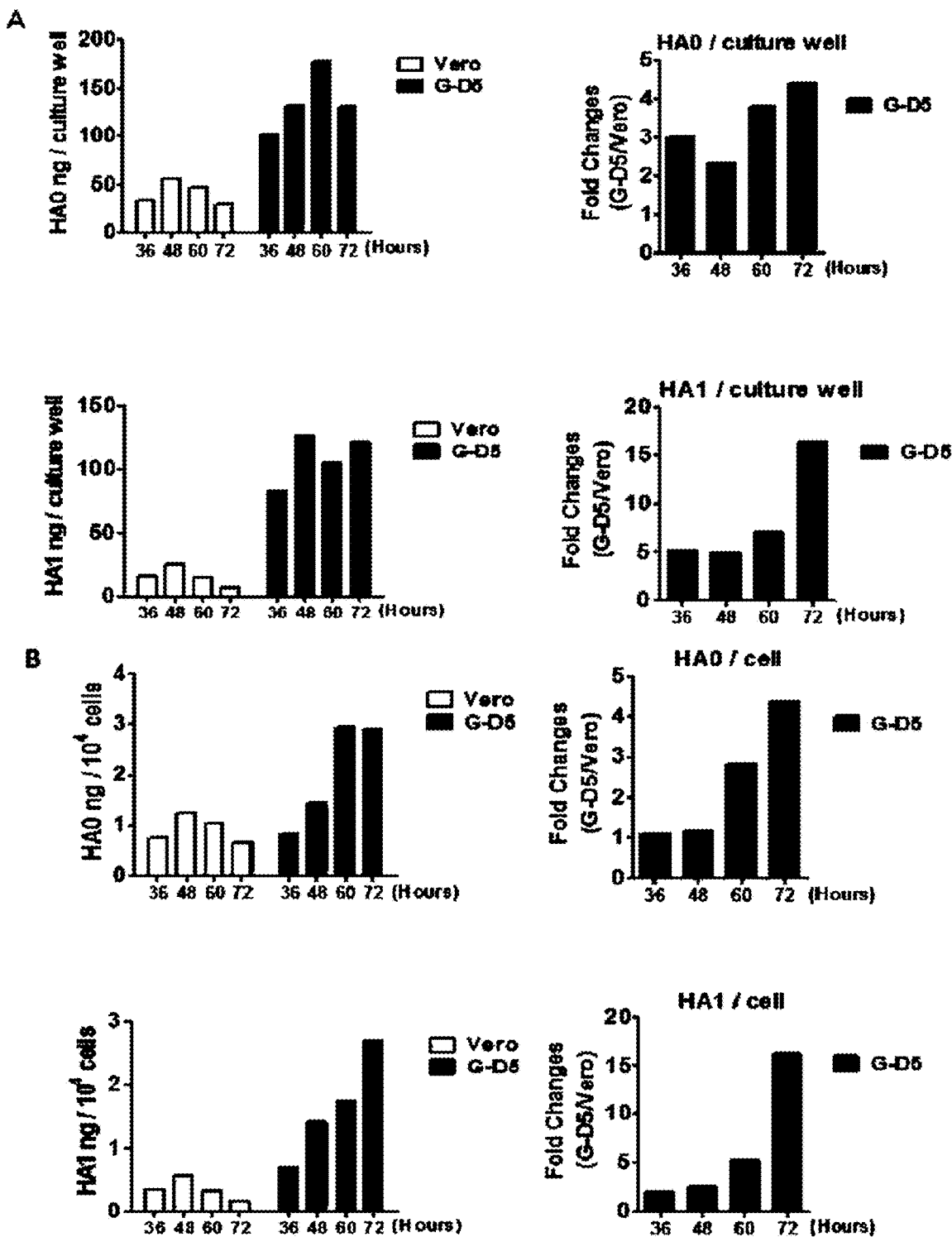
FIG. 5 shows the results of comparing the increase in intracellular viral antigenic proteins per culture well and per cells between a wild-type Vero cell line and a G-D5 cell line lacking the function of Bst2 gene (A: viral antigenic proteins per culture well; B: viral antigenic proteins per cells).
Figure 6:
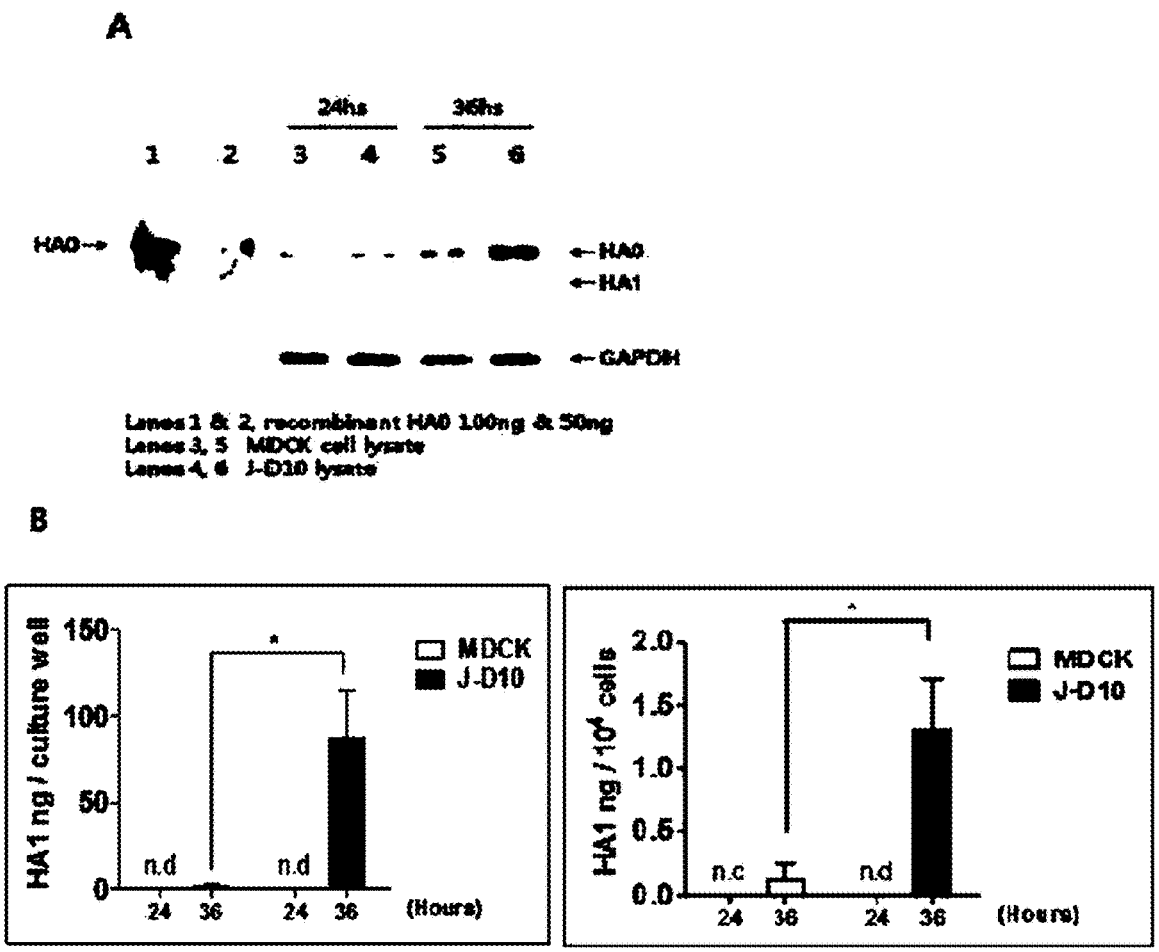
FIG. 6 shows the results of comparing the increase in intracellular viral antigenic proteins in total cell lysates and per cells between a wild-type MDCK cell line and a J-D10 cell line lacking the function of Bst2 gene (A: viral antigenic proteins in total cell lysates; B: intracellular viral antigenic protein per cells).

As a result, it was shown that the amount of influenza virus protein in the G-D5 cells lacking the function of Bst2 gene was about 5 times larger at 36 hours after infection, and about 15 times larger at 72 hours after infection, compared to that in the wild-type cells (FIG. 5, panel A). In addition, it was shown that the amount of influenza virus protein in the J-D10 cells lacking the function of Bst2 gene was about 57 times larger at 36 hours after infection (FIG. 6, panel B).

3-2: Human 293T Cell Line

To confirm the effect of increasing the production of viral antigenic protein by removal of the function of Bst2 gene from human cells, Bst2 gene knockout 293T cells (B4, B24 and D19, $2.5\times10^5$ cell/well) were infected with 0.01 MOI of H3N2 (A/Brisbane/10/2007) influenza cells in a 24-well plate for 30 minutes, and then cultured in a fresh medium for 2 days.

Figure 7:
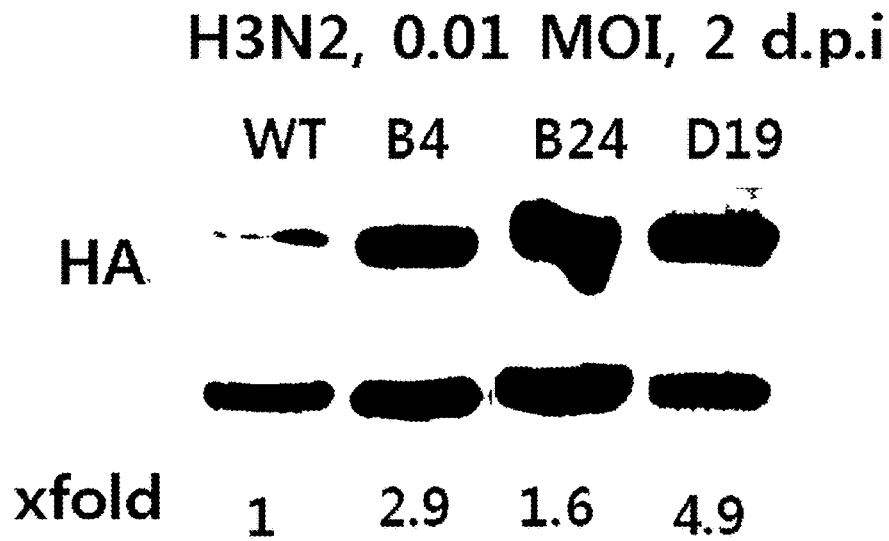
FIG. 7 shows the results of comparing the increase in a viral antigenic protein in a human 293T cell line lacking the function of Bst2 gene.

As a result, it was shown by Western blot analysis that the amount of viral protein in the Bst2 gene knockout 293T cells significantly increased, like those in Vero and MDCK cell lines (FIG. 7).

Release of virus from a cell line lacking the function of Bst2 gene is effectively achieved. Thus, if the growth rate of virus in cells lacking the function of Bst2 gene is the same as that in wild-type cells and if the release of virus from cells lacking the function of Bst2 gene is much faster than that from the wild-type cells, the amount of intracellular virus not released from the cells lacking the function of Bst2 gene is expected to be much more than that in the wild-type cells. However, the amount of virus released from the cells lacking the function of Bst2 gene and the amount of virus remaining in the cells also significantly increase.

Thus, the release of virus from the cells lacking the function of Bst2 gene and the growth of virus in the cells are promoted, indicating that the Bst2 protein can inhibit the growth of virus in host cells. Namely, it can be seen that the growth of a target virus in cells lacking the function of Bst2 can be promoted so that the production of virus and antigenic protein therein can be increased.

Example 4

Increase in the Amount of Intracellular Viral Proteins Per Cells Lacking the Function of Bst2 Gene In this Example, the amount of intracellular viral antigenic protein per cells lacking the function of Bst2 gene was analyzed. Because the apoptosis of cells lacking the function of Bst2 gene is effectively inhibited even when these cells are infected with virus, the results of Example 3, there can be a difference in cell number between wild-type cells and cells lacking the function of Bst2 gene, and for this reason, the amount of intracellular viral antigenic protein per cells was analyzed.

Specifically, wild-type Vero and MDCK cells and mutant cells ($5 \times 10^4$ cell/well) lacking the function of Bst2 were infected with 0.1 MOI of A/H3N2 influenza virus for 30 minutes, and then the medium was replaced with a fresh medium, followed by culture for 36-72 hours. At each time point, viruses released into the medium were removed, and cells remaining at the bottom of the culture flask were washed with PBS, and then harvested, after which the amount of cell lysate was per cells ($1 \times 10^6$ cells/ml). Cell lysate corresponding to $10^4$ cells was electrophoresed by SDS-PAGE, and then analyzed by Western blotting with anti-HA monoclonal antibody that recognizes large fragments of influenza virus HA proteins.

As a result, it was shown that the amount of intracellular influenza virus protein per cells in the G-D5 cells lacking the function of Bst2 gene was about two times larger at 36 hours after infection, and about 17 times larger at 72 hours after infection, compared to that in the wild-type cells (FIG. 5, panel B). In addition, it was shown that the amount of intracellular influenza virus protein per cells in the J-D10 cells lacking the function of Bst2 gene was about 7 times larger at 36 hours after infection compared to that in the wild-type cells (FIG. 6, panel B).

This indicates that the amount of influenza virus contained in the same number of cells is larger in cells lacking the function of Bst2 gene than in wild-type cells. Thus, it was found that the growth of virus in a cell line lacking the function of Bst2 gene is promoted, suggesting that the Bst2 protein can inhibit the growth of virus in host cells. Namely, it can be seen that cells lacking the function of Bst2 can produce virus and protein in increased amounts by promoting the growth of a target virus therein.

INDUSTRIAL APPLICABILITY

As described above, the inventive methods for promoting an infection of a target virus and increasing a production of the target protein by use of an animal cell line lacking the function of Bst2 gene can increase the production yields of the target virus and antigenic protein, and thus are useful for the production of vaccines for the prevention or treatment of viral diseases.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

The invention claimed is:

1. A method for promoting an infection in a mammalian cell line that is permissive to a target virus, the method comprising:

preparing a virus-producing mutant cell line which lacks the function of a Bst-2 gene by deleting or inserting specific nucleotides from or into exon1 region of the Bst2 gene comprising the nucleotide sequence of SEQ ID NOS: 1, 2 or 24, wherein the cell line is selected from the group consisting of MDCK (Madin-Darby Canine Kidney), Vero and 293T human cell, and wherein the mutant cell line:

(i) comprises the sequence in exon I region of the Bst2 gene selected from the group consisting of SEQ ID NOS: 3 to 10, 17 to 21, 25, and 27; or (ii) consists of the sequence in exon I region of the Bst2 gene selected from the group consisting of SEQ ID NOS: 26, 28, 29, and 30; and infecting the mutant cell line with the target virus, wherein the mutant cell line exhibits an increased ability to produce the target virus by lacking the function of said Bst-2 gene.

2. A method for producing a target virus in a mammalian cell line that is permissive to said target virus, the method comprising:

preparing a virus-producing mutant cell line which lacks the function of a Bst-2 gene by deleting or inserting specific nucleotides from or into exon1 region of the Bst2 gene comprising the nucleotide sequence of SEQ ID NOS: 1, 2 or 24, wherein the cell line is selected from the group consisting of MDCK (Madin-Darbv Canine Kidney), Vero and 293T human cell, and wherein the mutant cell line:
  (i) comprises the sequence in exon I region of the Bst2 gene selected from the group consisting of SEQ ID NOS: 3 to 10, 17 to 21, 25, and 27; or
  (ii) consists of the sequence in exon I region of the Bst2 gene selected from the group consisting of SEQ ID NOS: 26, 28, 29, and 30;

infecting the mutant cell line with the target virus; and
culturing the infected mutant cell line; wherein the mutant cell line exhibits an increased ability to produce the target virus by lacking the function of said Bst-2 gene.

3. A method for producing an antigenic protein of a target virus in a mammalian cell line that is permissive to said target virus, the method comprising:

preparing a virus-producing mutant cell line which lacks the function of a Bst-2 gene by deleting or inserting specific nucleotides from or into exon1 region of the Bst2 gene comprising the nucleotide sequence of SEQ ID NOS: 1, 2 or 24, wherein the cell line is selected from the group consisting of MDCK (Madin-Darbv Canine Kidney), Vero and 293T human cell, and wherein the mutant cell line:
  (i) comprises the sequence in exon I region of the Bst2 gene selected from the group consisting of SEQ ID NOS: 3 to 10, 17 to 21, 25, and 27; or
  (ii) consists of the sequence in exon I region of the Bst2 gene selected from the group consisting of SEQ ID NOS: 26, 28, 29, and 30;

infecting the mutant cell line with the target virus;
culturing the infected mutant cell line to amplify intracellularly said target virus; and
obtaining the intracellular viral protein from a cell lysate of the cultured mutant cell line, thereby producing the antigenic protein; wherein the mutant cell line exhibits an increased ability to produce the target virus by lacking the function of said Bst-2 gene.

4. The method of claim 3, wherein the virus is an enveloped or naked virus.

5. The method of claim 4, wherein the enveloped virus is influenza or herpesvirus.

6. The method of claim 3, wherein the virus is a DNA or RNA virus.

7. The method of claim 3, wherein the cell line is infected with the target virus at an MOI (multiplicity of infection) of 0.0001-0.1.

8. The method of claim 3, wherein the cell line is infected at a cell density of $1 \times 10^4$ to $1 \times 10^7$ cells/ml.

9. The method of claim 3, wherein, wherein the infection of the cell line is performed under a 5% $CO_2$ condition at 37° C.

10. The method of claim 1, wherein the exon1 region of Bst2 (bone marrow stromal cell antigen 2) gene encodes the cytoplasmic domain of Bst2 protein.

11. The method of claim 2, wherein the exon1 region of Bst2 (bone marrow stromal cell antigen 2) gene encodes the cytoplasmic domain of Bst2 protein.

12. The method of claim 3, wherein the exon1 region of Bst2 (bone marrow stromal cell antigen 2) gene encodes the cytoplasmic domain of Bst2 protein.

* * * * *

SEQUENCE LISTING

```
<160> NUMBER OF SEQ ID NOS: 30

<210> SEQ ID NO 1
<211> LENGTH: 306
<212> TYPE: DNA
<213> ORGANISM: dog

<400> SEQUENCE: 1
atggcaccta cgctttacca ctactactgg cctgtgccca taactgacga gtcagagtca      60
atgtcatcaa gtcagaagct gagctggctg gagtggctgg gcatcttggg gatcccagtg     120
gtgatgggtc tgtctgtggc tctgatcatc tttgttgtca agaccaacag caaagcctgc     180
ggggatggcc tcctagtaga gcaggagtgt cacaatgtca ccagcctcct ggagcgccaa     240
ctaacccaaa cccggcaagc gttacagggg accatggacc aggctaccac ctgcaacaag     300
actgtg                                                                306

<210> SEQ ID NO 2
<211> LENGTH: 294
<212> TYPE: DNA
<213> ORGANISM: monkey

<400> SEQUENCE: 2
atggcaccta ttttgtatga ctattgcaaa atgcccatgg atgacatttg caaggaagac      60
agggacaagt gctgtaaact ggccgtagga attctggggc tcctggtcat agtgcttctg     120
ggggtgcccc tgatttttctt catcatcaag gccaacagcg aggcctgcca ggatggcctc     180
```
cgggcagtga tggagtgtca caatgtcacc tatctcctgc aacaagagct ggccgaggcc    240
cagcggggct ttcgggacgc agaggcccag gctgtcacct gcaaccagac tgtg           294

<210> SEQ ID NO 3
<211> LENGTH: 304
<212> TYPE: DNA
<213> ORGANISM: dog

<400> SEQUENCE: 3
atggcaccta cgctttacca ctactactgg cctgtgccca taactgaagt cagagtcaat    60
gtcatcaagt cagaagctga gctggctgga gtggctgggc atcttgggga tcccagtggt    120
gatgggtctg tctgtggctc tgatcatctt tgttgtcaag accaacagca aagcctgcgg    180
ggatggcctc ctagtagagc aggagtgtca caatgtcacc agcctcctgg agcgccaact    240
aacccaaacc cggcaagcgt tacaggggac catggaccag gctaccacct gcaacaagac    300
tgtg                                                                 304

<210> SEQ ID NO 4
<211> LENGTH: 304
<212> TYPE: DNA
<213> ORGANISM: dog

<400> SEQUENCE: 4
atggcaccta cgctttacca ctactactgg cctgtgccca taacacgagt cagagtcaat    60
gtcatcaagt cagaagctga gctggctgga gtggctgggc atcttgggga tcccagtggt    120
gatgggtctg tctgtggctc tgatcatctt tgttgtcaag accaacagca aagcctgcgg    180
ggatggcctc ctagtagagc aggagtgtca caatgtcacc agcctcctgg agcgccaact    240
aacccaaacc cggcaagcgt tacaggggac catggaccag gctaccacct gcaacaagac    300
tgtg                                                                 304

<210> SEQ ID NO 5
<211> LENGTH: 302
<212> TYPE: DNA
<213> ORGANISM: dog

<400> SEQUENCE: 5
atggcaccta cgctttacca ctactactgg cctgtgccca taactagtca gagtcaatgt    60
catcaagtca gaagctgagc tggctggagt ggctgggcat cttggggatc ccagtggtga    120
tgggtctgtc tgtggctctg atcatctttg ttgtcaagac caacagcaaa gcctgcgggg    180
atggcctcct agtagagcag gagtgtcaca atgtcaccag cctcctggag cgccaactaa    240
cccaaacccg gcaagcgtta caggggacca tggaccaggc taccacctgc aacaagactg    300
tg                                                                   302

<210> SEQ ID NO 6
<211> LENGTH: 303
<212> TYPE: DNA
<213> ORGANISM: dog

<400> SEQUENCE: 6
atggcaccta cgctttacca ctactactgg cctgtgccca taactgagtc agagtcaatg    60
tcatcaagtc agaagctgag ctggctggag tggctgggca tcttggggat cccagtggtg    120
atgggtctgt ctgtggctct gatcatcttt gttgtcaaga ccaacagcaa agcctgcggg    180

```
gatggcctcc tagtagagca ggagtgtcac aatgtcacca gcctcctgga gcgccaacta    240
acccaaaccc ggcaagcgtt acaggggacc atggaccagg ctaccacctg caacaagact    300
gtg                                                                  303

<210> SEQ ID NO 7
<211> LENGTH: 302
<212> TYPE: DNA
<213> ORGANISM: dog

<400> SEQUENCE: 7
atggcaccta cgctttacca ctactactgg cctgtgccca taacgagtca gagtcaatgt     60
catcaagtca gaagctgagc tggctggagt ggctgggcat cttggggatc ccagtggtga    120
tgggtctgtc tgtggctctg atcatctttg ttgtcaagac aacagcaaa gcctgcgggg     180 atggcctcct agtagagcag gagtgtcaca atgtcaccag cctcctggag cgccaactaa    240
cccaaacccg gcaagcgtta caggggacca tggaccaggc taccacctgc aacaagactg    300
tg                                                                   302

<210> SEQ ID NO 8
<211> LENGTH: 309
<212> TYPE: DNA
<213> ORGANISM: dog

<400> SEQUENCE: 8
atggcaccta cgctttacca ctactactgg cctgtgccca taactgacga cgagtcagag     60
tcaatgtcat caagtcagaa gctgagctgg ctggagtggc tgggcatctt ggggatccca    120
gtggtgatgg gtctgtctgt ggctctgatc atctttgttg tcaagaccaa cagcaaagcc    180
tgcggggatg gcctcctagt agagcaggag tgtcacaatg tcaccagcct cctggagcgc    240
caactaaccc aaacccggca agcgttacag gggaccatgg accaggctac cacctgcaac    300
aagactgtg                                                            309

<210> SEQ ID NO 9
<211> LENGTH: 282
<212> TYPE: DNA
<213> ORGANISM: monkey

<400> SEQUENCE: 9
atggcaccta ttttgtatga ctattgcaaa atgcccatgg atgacatttg caaggaagac     60
agggacaagt gctgtaaact ggccgtagga attctggggc tcctggtcat agtgccctg     120 attttcttca tcatcaaggc caacagcgag gcctgccagg atggcctccg ggcagtgatg    180
gagtgtcaca atgtcaccta tctcctgcaa caagagctgg ccgaggccca gcggggcttt    240
cgggacgcag aggcccaggc tgtcacctgc aaccagactg tg                       282

<210> SEQ ID NO 10
<211> LENGTH: 293
<212> TYPE: DNA
<213> ORGANISM: monkey

<400> SEQUENCE: 10
atggcaccta ttttgtatga ctattgcaaa atgcccatgg atgacatttg caaggaagac     60
agggacaagt gctgtaaact ggccgtagga attctggggc tcctggtcat agtgcttctg    120
ggggtgccct gattttcttc atcatcaagg ccaacagcga ggcctgccag gatggcctcc    180 ggcagtgat ggagtgtcac aatgtcacct atctcctgca acaagagctg gccgaggccc    240
```
agcggggctt tcgggacgca gaggcccagg ctgtcacctg caaccagact gtg    293

```
<210> SEQ ID NO 11
<211> LENGTH: 20
<212> TYPE: DNA
<213> ORGANISM: Artificial Sequence
<220> FEATURE:
<223> OTHER INFORMATION: dBst2-F primer

<400> SEQUENCE: 11
```
ggtcaggatg gctcctatgc    20

```
<210> SEQ ID NO 12
<211> LENGTH: 20
<212> TYPE: DNA
<213> ORGANISM: Artificial Sequence
<220> FEATURE:
<223> OTHER INFORMATION: dBst2-R primer

<400> SEQUENCE: 12
```
aacctgacag ggtcacctgg    20

```
<210> SEQ ID NO 13
<211> LENGTH: 21
<212> TYPE: DNA
<213> ORGANISM: Artificial Sequence
<220> FEATURE:
<223> OTHER INFORMATION: NdBst2-F primer

<400> SEQUENCE: 13
```
gtagccccag ccaaaggttt c    21

```
<210> SEQ ID NO 14
<211> LENGTH: 20
<212> TYPE: DNA
<213> ORGANISM: Artificial Sequence
<220> FEATURE:
<223> OTHER INFORMATION: NdBst2-R primer

<400> SEQUENCE: 14
```
aggcctcccc atgcccaaac    20

```
<210> SEQ ID NO 15
<211> LENGTH: 19
<212> TYPE: DNA
<213> ORGANISM: Artificial Sequence
<220> FEATURE:
<223> OTHER INFORMATION: AGM-F primer

<400> SEQUENCE: 15
``` gaggggaga tctggatgg    19

```
<210> SEQ ID NO 16
<211> LENGTH: 20
<212> TYPE: DNA
<213> ORGANISM: Artificial Sequence
<220> FEATURE:
<223> OTHER INFORMATION: AGM-R primer

<400> SEQUENCE: 16
```
aggcctcccc atgcccaaac    20

```
<210> SEQ ID NO 17
<211> LENGTH: 573
<212> TYPE: DNA
```

<213> ORGANISM: dog

<400> SEQUENCE: 17

| | | | | | |
|---|---|---|---|---|---|
| atggcaccta | cgctttacca | ctactactgg | cctgtgccca | taactgacct | atgagagtca | 60 |
| gagtcaatgt | catcaagtca | gaagctgagc | tggctggagt | ggctgggcat | cttggggatc | 120 |
| ccagtggtga | tgggtctgtc | tgtggctctg | atcatctttg | ttgtcaagac | caacagcaaa | 180 |
| gcctgcgggg | atggcctcct | agtagagcag | gagtgtcaca | atgtcaccag | cctcctggag | 240 |
| cgccaactaa | cccaaacccg | gcaagcgtta | caggggacca | tggaccaggc | taccacctgc | 300 |
| aacaagactg | tggtgaccct | gtcagcttcc | ctggtgaagg | agaaggcctg | ggtcaggag | 360 |
| cagctcaccc | gaggagagaa | acttcaggga | gagatcgaga | cattgaagca | gcagctgcag | 420 |
| gccgctttgg | aggaggtgaa | gcagctaaga | gaagggaagg | aggcctcaag | caaggaaagg | 480 |
| gaaaccagct | ccgtcagctc | cttgaaggca | ccccccggct | ccgtggtggt | ccccgtgtac | 540 |
| ctgctcctag | gccttagggc | tctgctggcc | tga | | | 573 |

<210> SEQ ID NO 18
<211> LENGTH: 564
<212> TYPE: DNA
<213> ORGANISM: dog

<400> SEQUENCE: 18

| | | | | | |
|---|---|---|---|---|---|
| atggcaccta | cgctttacca | ctactactgg | cctgtgccca | taactgagtc | agagtcaatg | 60 |
| tcatcaagtc | agaagctgag | ctggctggag | tggctgggca | tcttggggat | cccagtggtg | 120 |
| atgggtctgt | ctgtggctct | gatcatcttt | gttgtcaaga | ccaacagcaa | agcctgcggg | 180 |
| gatggcctcc | tagtagagca | ggagtgtcac | aatgtcacca | gcctcctgga | gcgccaacta | 240 |
| acccaaaccc | ggcaagcgtt | acaggggacc | atggaccagg | ctaccacctg | caacaagact | 300 |
| gtggtgaccc | tgtcagcttc | cctggtgaag | gagaaggcct | ggggtcagga | gcagctcacc | 360 |
| cgaggagaga | aacttcaggg | agagatcgag | acattgaagc | agcagctgca | ggccgctttg | 420 |
| gaggaggtga | agcagctaag | agaagggaag | gaggcctcaa | gcaaggaaag | ggaaaccagc | 480 |
| tccgtcagct | ccttgaaggc | accccccggc | tccgtggtgg | tccccgtgta | cctgctccta | 540 |
| ggccttaggg | ctctgctggc | ctga | | | | 564 |

<210> SEQ ID NO 19
<211> LENGTH: 566
<212> TYPE: DNA
<213> ORGANISM: dog

<400> SEQUENCE: 19

| | | | | | |
|---|---|---|---|---|---|
| atggcaccta | cgctttacca | ctactactgg | cctgtgccca | taactgagag | tcagagtcaa | 60 |
| tgtcatcaag | tcagaagctg | agctggctgg | agtggctggg | catcttgggg | atcccagtgg | 120 |
| tgatgggtct | gtctgtggct | ctgatcatct | ttgttgtcaa | gaccaacagc | aaagcctgcg | 180 |
| gggatggcct | cctagtagag | caggagtgtc | acaatgtcac | cagcctcctg | gagcgccaac | 240 |
| taacccaaac | ccggcaagcg | ttacagggga | ccatggacca | ggctaccacc | tgcaacaaga | 300 |
| ctgtggtgac | cctgtcagct | tccctggtga | aggagaaggc | ctggggtcag | gagcagctca | 360 |
| cccgaggaga | gaaacttcag | ggagagatcg | agacattgaa | gcagcagctg | caggccgctt | 420 |
| tggaggaggt | gaagcagcta | agagaaggga | aggaggcctc | aagcaaggaa | agggaaacca | 480 |
| gctccgtcag | ctccttgaag | gcaccccccg | gctccgtggt | ggtccccgtg | tacctgctcc | 540 |
| taggccttag | ggctctgctg | gcctga | | | | 566 |

<210> SEQ ID NO 20
<211> LENGTH: 557
<212> TYPE: DNA
<213> ORGANISM: dog

<400> SEQUENCE: 20

| | | | | | |
|---|---|---|---|---|---|
| atggcaccta | cgctttacca | ctactactgg | cctgtgccca | taaagagtca | atgtcatcaa | 60 |
| gtcagaagct | gagctggctg | gagtggctgg | gcatcttggg | gatcccagtg | gtgatgggtc | 120 |
| tgtctgtggc | tctgatcatc | tttgttgtca | agaccaacag | caaagcctgc | ggggatggcc | 180 |
| tcctagtaga | gcaggagtgt | cacaatgtca | ccagcctcct | ggagcgccaa | ctaacccaaa | 240 |
| cccggcaagc | gttacagggg | accatggacc | aggctaccac | ctgcaacaag | actgtggtga | 300 |
| ccctgtcagc | ttccctggtg | aaggagaagg | cctggggtca | ggagcagctc | acccgaggag | 360 |
| agaaacttca | gggagagatc | gagacattga | agcagcagct | gcaggccgct | ttggaggagg | 420 |
| tgaagcagct | aagagaaggg | aaggaggcct | caagcaagga | aagggaaacc | agctccgtca | 480 |
| gctccttgaa | ggcaccccccc | ggctccgtgg | tggtccccgt | gtacctgctc | ctaggcctta | 540 |
| gggctctgct | ggcctga | | | | | 557 |

<210> SEQ ID NO 21
<211> LENGTH: 561
<212> TYPE: DNA
<213> ORGANISM: dog

<400> SEQUENCE: 21

| | | | | | |
|---|---|---|---|---|---|
| atggcaccta | cgctttacca | ctactactgg | cctgtgccca | tagacgaaga | gtcaatgtca | 60 |
| tcaagtcaga | agctgagctg | gctggagtgg | ctgggcatct | ggggatccc | agtggtgatg | 120 |
| ggtctgtctg | tggctctgat | catctttgtt | gtcaagacca | cagcaaagc | ctgcggggat | 180 |
| ggcctcctag | tagagcagga | gtgtcacaat | gtcaccagcc | tcctggagcg | ccaactaacc | 240 |
| caaacccggc | aagcgttaca | ggggaccatg | gaccaggcta | ccacctgcaa | caagactgtg | 300 |
| gtgaccctgt | cagcttccct | ggtgaaggag | aaggcctggg | gtcaggagca | gctcacccga | 360 |
| ggagagaaac | ttcagggaga | gatcgagaca | ttgaagcagc | agctgcaggc | cgctttggag | 420 |
| gaggtgaagc | agctaagaga | agggaaggag | gcctcaagca | aggaaaggga | aaccagctcc | 480 |
| gtcagctcct | tgaaggcacc | ccccggctcc | gtggtggtcc | ccgtgtacct | gctcctaggc | 540 |
| cttagggctc | tgctggcctg | a | | | | 561 |

<210> SEQ ID NO 22
<211> LENGTH: 20
<212> TYPE: DNA
<213> ORGANISM: Artificial Sequence
<220> FEATURE:
<223> OTHER INFORMATION: HBst2-F1 primer

<400> SEQUENCE: 22
tggcacggcc taggcactca                                              20

<210> SEQ ID NO 23
<211> LENGTH: 20
<212> TYPE: DNA
<213> ORGANISM: Artificial Sequence
<220> FEATURE:
<223> OTHER INFORMATION: HBst2-R1 primer

<400> SEQUENCE: 23
ggatactgag gtccccgatt                                                  20

<210> SEQ ID NO 24
<211> LENGTH: 1881
<212> TYPE: DNA
<213> ORGANISM: human

<400> SEQUENCE: 24
atggcatcta cttcgtatga ctattgcaga gtgcccatgg aagacgggga taagcgctgt      60
aagcttctgc tggggatagg aattctggtg ctcctgatca tcgtgattct ggggggtgccc    120
ttgattatct tcaccatcaa ggccaacagc gaggcctgcc gggacggcct tcgggcagtg    180
atggagtgtc gcaatgtcac ccatctcctg caacaagagc tgaccgaggc ccagaagggc    240
tttcaggatg tggaggccca ggccgccacc tgcaaccaca ctgtggtaag ctcctcaact    300
cctttggatg gcctagtact aggcggtggg agggacaaga atctctcccc agaaatctga    360
cccagggtgg gtctccaggg agatgcaggg gaggtcctga aactgctcct gggccccac    420
atcaagggac ctaggttccc ctaccagggt ttgtgggccc ctaacccagt ccagggcact    480
ggtgtagggg cagggtgtta aaactctcca gatcccccaa atcggggacc tcagtatccc    540
cctgggactt aggtgaattt ataaattctt tccaggcac tggtgtcggg ggccttgaaa     600
ctcctcgtgg gcaccagtcc tgggggagta gaaatcccta ttcagggttg aaggggggacc   660
tcaccagacc ctgaaaaagg gggcttttga aattttcact tcatccctaa gaaactgaaa    720
tattcacctg ggtcctgata tgggggatct tgaaactctc gctgggcatg tcacttgggc    780
ggggaaatcc cactgcattc tggatttggt agggccctct aacttttctt gggccattgc    840
tcaggcaatc tggaaatgtc cactaaactt tggttatcga tagcctccaa gtttccacgt    900
ggggtggcct caaaactccc attttgagga cccacatgct tatgggtggc ctgggagag    960
tgtgtggttg tggctgttct ttaaggttgg agaccatggt gcagagaggg ttggaagaaa   1020
acctgaaagg ggtttgcatt taagcccctc tgtccccagg acctagggag gaggcccagg   1080
tcccagggggc agcagccaaa ctccccaggc caaaaccca gattctaact cttcttagat   1140
ggccctaatg gcttccctgg atgcagagaa ggcccaagga caaagaaag tggaggagct    1200
tgagggtgag aaagggagaa gggagagggc cggggagggg tgagtcaggt atggaagagg   1260
gggtgggggc agggagacca gggctggagg ttggggtaag gggaggttc tgtcccagag    1320
tggagcaggg ccccagcatg ccacatgct gacccgcccc ctgtttctgt cctcccaccc   1380
taccaggaga gatcactaca ttaaaccata agcttcagga gcgtctgca gaggtggagc   1440
gactgaggtc agagatagcc ttccccccgct accctccacc tgccacattc ctctcacccc   1500
cacatcccta gcccaagacc caggatctcc tttgctccca aaatccccat gccccaagg    1560
gataaagttt gagtcccaca aaaggataac ttagccccta gggtcacaga gccatgggtg   1620
gccgctgtcc attccctccc cggtgacttg gattggggcg gtgcggggg aactcccggg    1680
ggcggtgggc ttacagggag gcgcagcagga gccaggacga gcagatgcct gatttgccat   1740
ctgtaccgca gaagagaaaa ccaggtctta agcgtgagaa tcgcggacaa gaagtactac   1800
cccagctccc aggactccag ctccgctgcg gcgccccagc tgctgattgt gctgctgggc   1860
ctcagcgctc tgctgcagtg a                                             1881

<210> SEQ ID NO 25
<211> LENGTH: 61
<212> TYPE: DNA
<213> ORGANISM: human

```
<400> SEQUENCE: 25
atggcatcta cttcgtatga ctattgcaga gtgcccatgg aagacgggga gataggaatt    60
c                                                                    61

<210> SEQ ID NO 26
<211> LENGTH: 85
<212> TYPE: DNA
<213> ORGANISM: human

<400> SEQUENCE: 26
atggcatcta cttcgtatga ctattgcaga gtgcccatgg aagacgggga taagcgctgt    60
aagcttctgc tggggatagg aattc                                          85

<210> SEQ ID NO 27
<211> LENGTH: 86
<212> TYPE: DNA
<213> ORGANISM: human

<400> SEQUENCE: 27
atggcatcta cttcgtatga ctattgcaga gtgcccatgg aagacgggga taagcgctgt    60
aagcttcttg ctggggatag gaattc                                         86

<210> SEQ ID NO 28
<211> LENGTH: 64
<212> TYPE: DNA
<213> ORGANISM: human

<400> SEQUENCE: 28
atggcatcta cttcgtatga ctattgcaga gtgcccatgg aagacgggga taagcgctgt    60
aagc                                                                 64

<210> SEQ ID NO 29
<211> LENGTH: 82
<212> TYPE: DNA
<213> ORGANISM: human

<400> SEQUENCE: 29
atggcatcta cttcgtatga ctattgcaga gtgcccatgg aagacgggga taagcgctgt    60
aagcttctgc tgataggaat tc                                             82

<210> SEQ ID NO 30
<211> LENGTH: 77
<212> TYPE: DNA
<213> ORGANISM: human

<400> SEQUENCE: 30
atggcatcta cttcgtatga ctattgcaga gtgcccatgg aagacgggga taagcgctgt    60
aatggggata ggaattc                                                   77
```